United States Patent

Ogawa et al.

(10) Patent No.: US 10,258,420 B2
(45) Date of Patent: Apr. 16, 2019

(54) SURGICAL MANIPULATOR SYSTEM

(71) Applicant: OLYMPUS CORPORATION, Tokyo (JP)

(72) Inventors: Ryohei Ogawa, Tokyo (JP); Masaru Yanagihara, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 204 days.

(21) Appl. No.: 15/244,228

(22) Filed: Aug. 23, 2016

(65) Prior Publication Data

US 2016/0354170 A1 Dec. 8, 2016

Related U.S. Application Data

(63) Continuation of application No. PCT/JP2015/055104, filed on Feb. 23, 2015.

(30) Foreign Application Priority Data

Feb. 25, 2014 (JP) .................................. 2014-034305

(51) Int. Cl.
*A61B 1/00* (2006.01)
*A61B 34/00* (2016.01)
(Continued)

(52) U.S. Cl.
CPC .............. *A61B 34/74* (2016.02); *A61B 34/30* (2016.02); *A61B 34/70* (2016.02); *A61B 90/98* (2016.02);
(Continued)

(58) Field of Classification Search
CPC . A61B 1/00059; A61B 1/00062; A61B 34/74; A61B 34/30; A61B 34/70; A61B 2034/301; A61B 90/98; A61B 2017/00212
See application file for complete search history.

(56) References Cited

U.S. PATENT DOCUMENTS

2004/0133189 A1 7/2004 Sakurai
2005/0119527 A1* 6/2005 Banik ................ A61B 1/00059
600/117
(Continued)

FOREIGN PATENT DOCUMENTS

EP 1 915 967 A1 4/2008
EP 2 014 218 A2 1/2009
(Continued)

OTHER PUBLICATIONS

International Search Report dated May 19, 2015 issued in corresponding Japanese Patent Application No. PCT/JP2015/055104.
(Continued)

*Primary Examiner* — Timothy J Neal
(74) *Attorney, Agent, or Firm* — Scully, Scott, Murphy & Presser, P.C.

(57) ABSTRACT

Provided is a surgical manipulator system including: a manipulator provided with a treatment tool having at least one joint and a drive portion that is attached to the treatment tool to drive the treatment tool; a manipulation input portion with which manipulation for causing, by driving the drive portion, the treatment tool to perform a desired operation is input; and a control portion that controls the drive portion on the basis of the manipulation that has been input via the manipulation input portion, wherein the treatment tool is provided with an identification-information retaining portion that retains identification information of the treatment tool, the manipulation input portion is provided with a
(Continued)

manipulation-side reading portion that performs short-distance communication with the identification-information retaining portion, thus reading the identification information of the treatment tool, and the control portion controls the drive portion based on the read identification information of the treatment tool.

10 Claims, 9 Drawing Sheets

(51) Int. Cl.
  *A61B 90/98* (2016.01)
  *A61B 34/30* (2016.01)
  *A61B 17/00* (2006.01)
  *A61B 90/00* (2016.01)

(52) U.S. Cl.
  CPC ........... *A61B 2017/00212* (2013.01); *A61B 2034/301* (2016.02); *A61B 2090/0803* (2016.02); *A61B 2090/0805* (2016.02); *A61B 2090/0806* (2016.02)

(56) References Cited

U.S. PATENT DOCUMENTS

| | | |
|---|---|---|
| 2005/0149003 A1 | 7/2005 | Tierney et al. |
| 2007/0213692 A1* | 9/2007 | Neubauer ............. A61B 34/20 606/1 |
| 2008/0262654 A1 | 10/2008 | Omori et al. |
| 2009/0018390 A1 | 1/2009 | Honda et al. |
| 2009/0062603 A1 | 3/2009 | Murakami et al. |
| 2016/0128547 A1 | 5/2016 | Ogawa et al. |

FOREIGN PATENT DOCUMENTS

| | | |
|---|---|---|
| EP | 2 033 590 A2 | 3/2009 |
| EP | 2 042 120 A2 | 4/2009 |
| EP | 3 025 629 A1 | 6/2016 |
| JP | 2001-125012 A | 5/2001 |
| JP | 2004-208922 A | 7/2004 |
| JP | 2008-104855 A | 5/2008 |
| JP | 2009-011809 A | 1/2009 |
| JP | 2009-061250 A | 3/2009 |
| JP | 2009-226028 A | 10/2009 |
| JP | 2010-022415 A | 2/2010 |
| JP | 2010-158303 A | 7/2010 |
| JP | 2015-024037 A | 2/2015 |
| WO | 2015/012163 A1 | 1/2015 |

OTHER PUBLICATIONS

Extended Supplementary European Search Report dated Oct. 9, 2017 in European Patent Application No. 15 75 5968.3.

* cited by examiner

SURGICAL MANIPULATOR SYSTEM

CROSS-REFERENCE TO RELATED APPLICATIONS

This is a continuation of International Application PCT/JP2015/055104, with an international filing date of Feb. 23, 2015, which is hereby incorporated by reference herein in its entirety. This application claims the benefit of Japanese Patent Application No. 2014-034305, the content of which is incorporated herein by reference.

TECHNICAL FIELD

The present invention relates to a surgical manipulator system.

BACKGROUND ART

In the related art, in surgical manipulator systems employing a master-slave system, there is a known surgical manipulator system in which a treatment tool to be attached to a slave-side drive portion in an attachable/detachable manner is provided with a memory storing identification information of the treatment tool, and in which the identification information of the attached treatment tool is transmitted to a control processor of the drive portion via an interface provided between the treatment tool and the drive portion (for example, see Patent Literature 1).

CITATION LIST

Patent Literature

{PTL 1} U.S. Patent Application, Publication No. 2005/0149003, Specification

SUMMARY OF INVENTION

Technical Problem

The present invention provides a surgical manipulator system with which it is possible to, without having to perform a bothersome setting operation and switching operation, intuitively associate a master to be manipulated and a treatment tool that a slave drives.

Solution to Problem

In order to achieve the above-described object, the present invention provides the following solutions.

A first aspect of the present invention is a surgical manipulator system including a manipulator provided with a treatment tool having at least one joint and a drive portion that is attached to the treatment tool to drive the treatment tool; a manipulation input portion with which manipulation for causing, by driving the drive portion of the manipulator, the treatment tool to perform desired operation is input; and a control portion that controls the drive portion on the basis of the manipulation that has been input via the manipulation input portion, wherein the treatment tool is provided with an identification-information retaining portion that retains identification information of the treatment tool, the manipulation input portion is provided with a manipulation-side reading portion that performs short-distance communication with the identification-information retaining portion of the treatment tool, thus reading the identification information of the treatment tool, and the control portion controls the drive portion on the basis of the identification information of the treatment tool read by the manipulation-side reading portion.

A second aspect of the present invention is a surgical manipulator system including a manipulator provided with a treatment tool having at least one joint and a drive portion that is attached to the treatment tool to drive the treatment tool; a manipulation input portion with which manipulation for causing, by driving the drive portion of the manipulator, the treatment tool to perform desired operation is input; and a control portion that controls the drive portion on the basis of the manipulation that has been input via the manipulation input portion, wherein the treatment tool is provided with an identification-information retaining portion that retains identification information of the treatment tool, the drive portion is provided with a main-unit-side reading portion that reads the identification information of the treatment tool, and retains main-unit identification information, which is the identification information of the drive portion, the manipulation input portion is provided with a manipulation-side reading portion that performs short-distance communication with the main-unit-side reading portion of the drive portion, thus reading the identification information of the treatment tool and the main-unit identification information, and the control portion controls the drive portion on the basis of the identification information of the treatment tool and the main-unit identification information read by the manipulation-side reading portion.

DESCRIPTION OF EMBODIMENTS

First Embodiment

A surgical manipulator system according to a first embodiment of the present invention will be described below with reference to the drawings.

Figure 1:
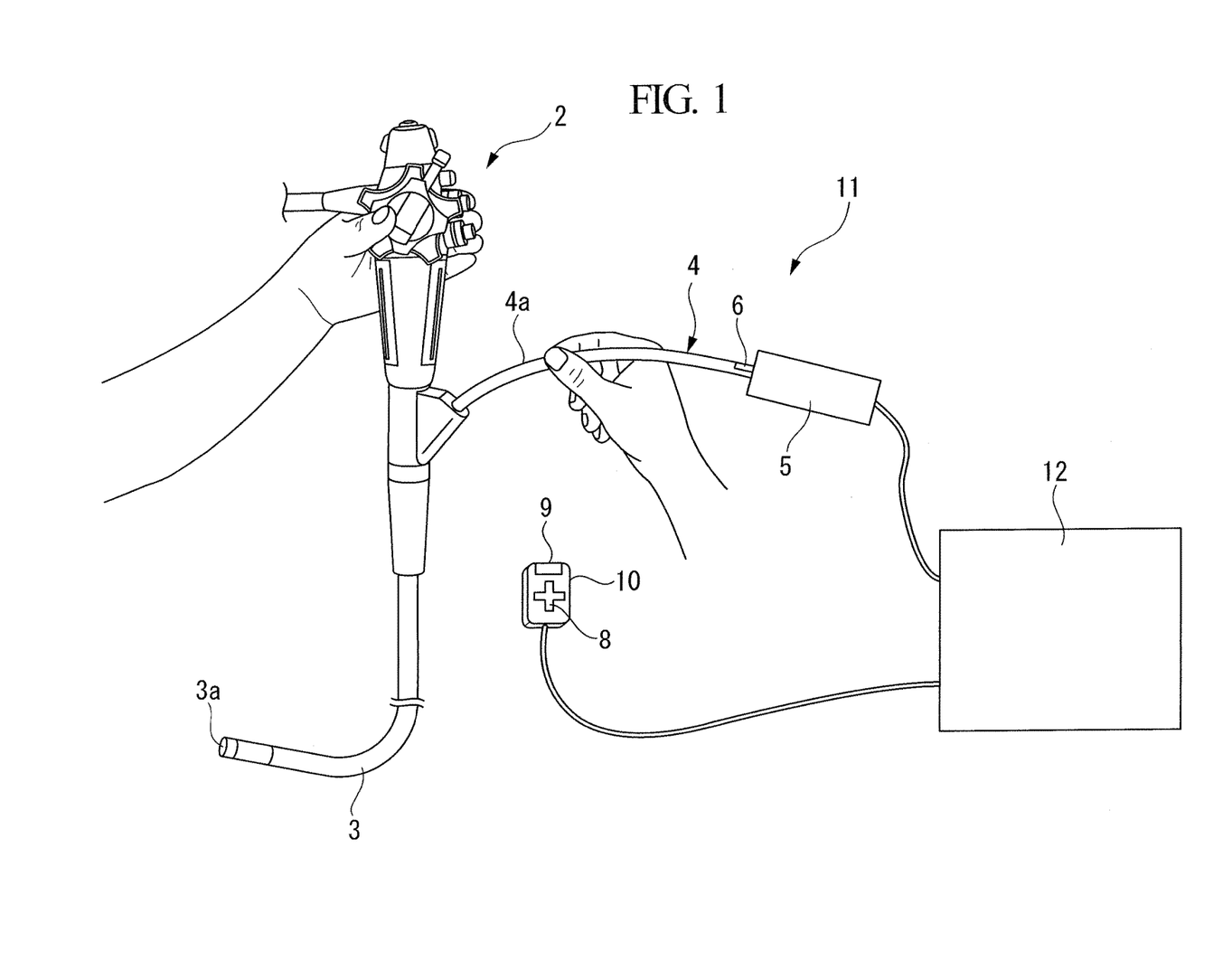
FIG. 1 is an overall configuration diagram showing a surgical manipulator system according to a first embodiment of the present invention.
Figure 2:
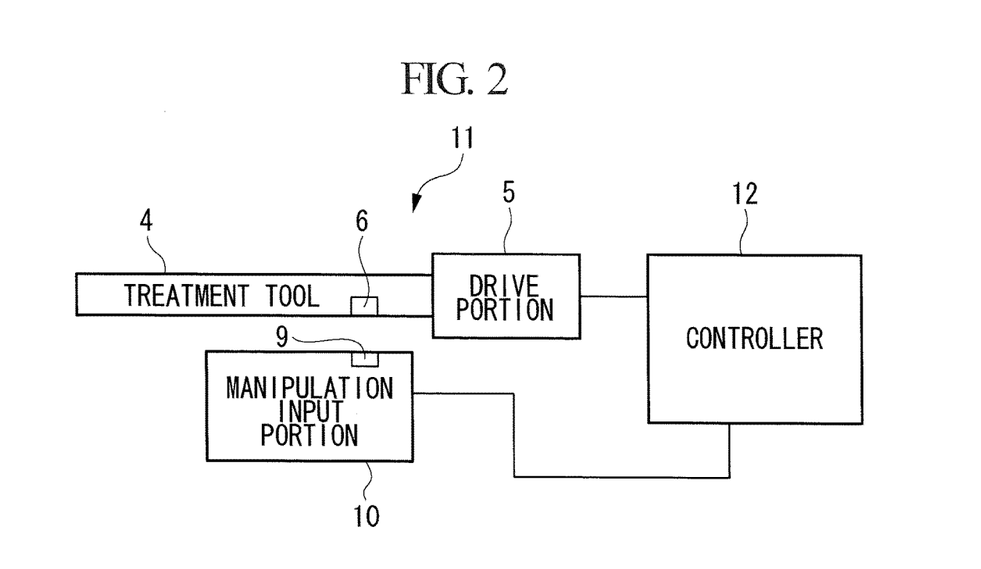
FIG. 2 is a diagram showing, in outline, the configuration of the surgical manipulator system according to the first embodiment of the present invention.

As shown in FIGS. 1 and 2, a surgical manipulator system according to this embodiment is a system with which manipulations by a surgeon are input in the form of instruction signals via a manipulation input portion 10, a controller (control portion) 12 controls a drive portion 5 of a manipulator 11 in accordance with the instruction signals on the basis of the manipulations of the manipulation input portion 10, and thus, a treatment tool 4 attached to the drive portion 5 is operated.

The manipulation input portion 10 is provided with a manipulating portion 8 with which manipulations by a surgeon are input in the form of instruction signals, and a manipulation-side reading portion 9 that reads, by performing short-distance communication with an identification-information retaining portion 6 (described later) of the treatment tool 4, the identification information of the treatment tool 4 from the identification-information retaining portion 6. The manipulation-side reading portion 9 reads the identification information of the treatment tool 4 and outputs the read identification information to the controller 12. The instruction signals input via the manipulating portion 8 are output to the controller 12. Various types of devices, such as a joystick, a dial, a four-way key, or the like, can be employed as the manipulating portion 8, and the controller 12 can associate the manipulating portion 8 of the manipulation input portion 10 in accordance with the treatment tool.

The manipulator 11 is provided with the treatment tool 4 that is inserted into a channel of an inserted portion 3 of an endoscope 2 and the drive portion 5 having a motor that drives the treatment tool 4. The treatment tool 4 has a flexible body portion 4a the length of which is sufficiently greater than that of the inserted portion 3, a joint (not shown) that is provided in the vicinity of a distal-end portion of the body portion 4a and that can be flexed, and an end effector (not shown) that is provided at the distal end of the body portion 4a and that is made to protrude from a distal-end surface 3a of the inserted portion 3. The treatment tool 4 has the identification-information retaining portion 6 that retains its own identification information and can be attached to and detached from the drive portion 5.

Note that conceivable identification information of the treatment tool 4 includes, for example, information unique to the treatment tool 4, which indicates the characteristics of that treatment tool 4, as well as, a serial number, production date, assembly factory, usage count (procedure, joint drive, energy), usage time, joint drive count, date and time of use, logs of connections with the system (manipulation input portion 10, drive portion 5, controller 12), hospital at which the treatment tool 4 is used, or the like for that treatment tool 4. Then, the controller 12 may store and manage the identification information of the treatment tool 4 in association with the treatment tool 4, and it is also possible to manage the identification information by storing it in a cloud computing system (not shown). In the case in which the identification information is managed by using the cloud computing system, there is an advantage in that, even in the case in which the treatment tool 4 is employed in another surgical manipulator system, it is possible to continue using the identification information of that treatment tool 4.

The controller 12 acquires the identification information of the treatment tool 4 from the manipulation-side reading portion 9, associates the manipulation input portion 10 and the drive portion 5 to which the treatment tool 4 is attached on the basis of the acquired identification information, and sets a control rule in accordance with the treatment tool 4. In other words, the controller 12 sets the correspondence relationship between the manipulation of the manipulation input portion 10 and the operation of the drive portion 5 to which the treatment tool 4 is attached, and also sets information required for control, such as the setting of control parameters in accordance with the identified treatment tool 4, speed switching of each joint, changes in kinematics solution, and so forth.

Figure 3:
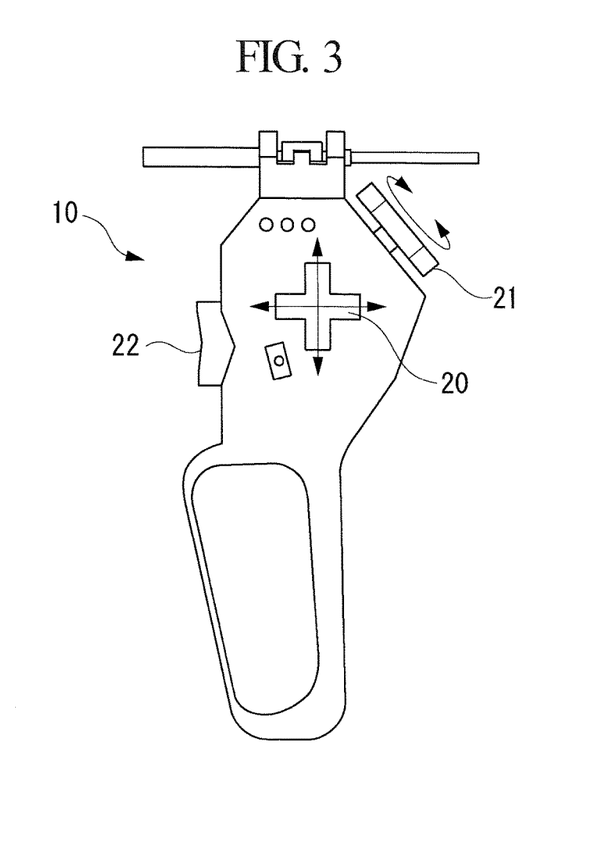
FIG. 3 is a diagram showing, in outline, the configuration of an example manipulation input portion employed in the surgical manipulator system according to the first embodiment of the present invention.

Regarding the correspondence relationship between the manipulation of the manipulation input portion 10 and the operation of the drive portion 5 to which the treatment tool 4 is attached, in the case in which the manipulation input portion 10 is provided with a four-way key 20, a rotation dial 21, and a trigger 22 as the manipulating portions 8, as shown in FIG. 3, the correspondence relationship between the manipulating portions 8 of the manipulation input portion 10 and the treatment tool 4 can be set, for example, as described below.

Figure 4A:
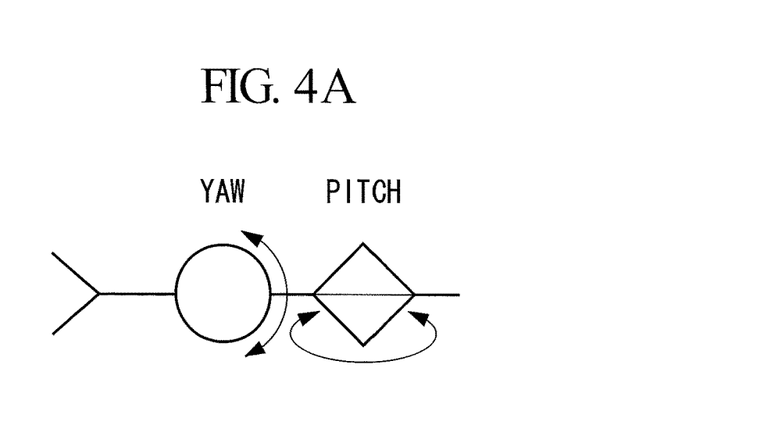
FIG. 4A is a schematic diagram showing example shaft configurations of a treatment tool that is compatible with the manipulation input portion in FIG. 3, in the cases in which yaw and pitch are included.

As shown in FIG. 4A, in the case in which the treatment tool 4 has two flexing joints for yaw and pitch, the rotation dial 21 is disabled, the individual joints are associated with the longitudinal direction and lateral direction of the four-way key 20, and the two joints are manipulated to be flexed via the manipulations of the four-way key 20.

Figure 4B:
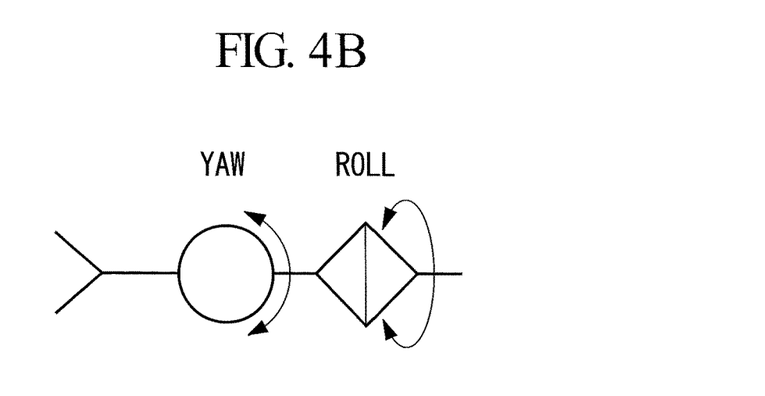
FIG. 4B is a schematic diagram showing example shaft configurations of a treatment tool that is compatible with the manipulation input portion in FIG. 3, in the cases in which yaw and roll are included.

As shown in FIG. 4B, in the case in which the treatment tool 4 has one rotating joint (roll) and one flexing joint (yaw), the rotating joint is associated with the rotation dial 21, and the flexing joint is associated with one direction of the four-way key 20, and the rotation dial 21 and the four-way key 20 are used to manipulate the rotation of the rotating joint and flexing of the flexing joint.

Figure 4C:
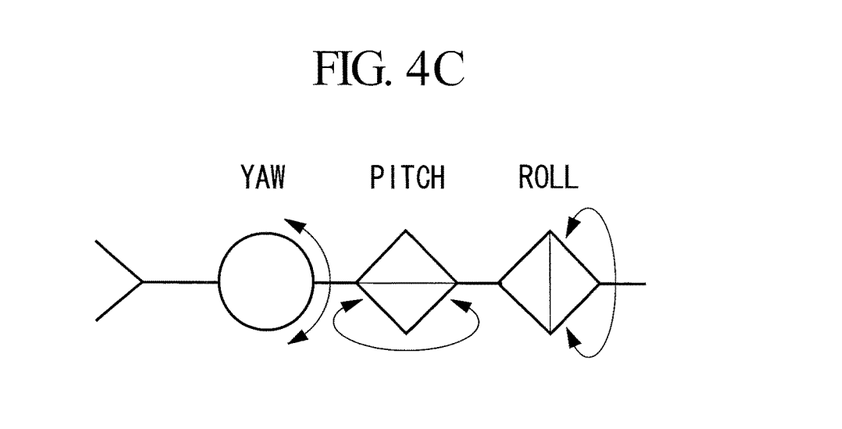
FIG. 4C is a schematic diagram showing example shaft configurations of a treatment tool that is compatible with the manipulation input portion in FIG. 3, in the cases in which yaw, pitch, and roll are included.

As shown in FIG. 4C, in the case in which the treatment tool 4 has two flexing joints for yaw and pitch and one rotating joint (roll), the individual joints are associated with the longitudinal direction and lateral direction of the four-way key 20, and the rotating joint is associated with the rotation dial 21. By doing so, the two joints are manipulated to be flexed via the manipulations of the four-way key 20, and the rotation dial 21 is used to manipulate the rotation of the rotating joint.

In addition, in the case in which the end effector of the treatment tool 4 is one of a gripper and energy or both, it is possible to associate the manipulating portions 8 of the manipulation input portion 10 and the treatment tool 4, for example, as described below.

Specifically, in the case in which the end effector of the treatment tool 4 is energy, the trigger 22 serves as a switch for the energy, and it is possible to turn on the energy by pressing in the trigger 22.

In the case in which the end effector of the treatment tool 4 is a gripper, the trigger 22 serves as a switch for the gripper, and it is possible to open or close the gripper by pressing the trigger 22.

In the case in which the end effectors of the treatment tool 4 are both a gripper and energy, while using the trigger 22 as a switch for both, the griper can be opened or closed by pressing the trigger 22, and the energy can be turned on when the trigger 22 is continued to be pressed for a certain amount of time or more. Alternatively, the switch for the energy can be associated with another button or the like.

Then, on the basis of the set correspondence relationship and the control rule, the controller 12 controls the drive portion 5 to which the treatment tool 4 is attached in accordance with the instruction signals from the manipulation input portion 10.

In order to perform desired treatment by using the thus-configured surgical manipulator system, prior to the treatment, the treatment tool 4 is attached to the drive portion 5, and the manipulation input portion 10, with which the manipulator 11 is manipulated, is brought close to the identification-information retaining portion 6 of the treatment tool 4. When brought close to the identification-information retaining portion 6, the manipulation-side reading portion 9 performs short-distance communication with the identification-information retaining portion 6, reads the identification information of the treatment tool 4 from the identification-information retaining portion 6, and outputs the read identification information to the controller 12.

In this way, with this embodiment, the controller 12 can ascertain the relationship between the manipulation input portion 10 and the treatment tool 4. In other words, because the controller 12 acquires the identification information of the treatment tool 4 from the manipulation-side reading portion 9, it is possible to ascertain the correspondence relationship between the manipulation input portion 10 and the drive portion 5 as well as the treatment tool 4, and it is also possible to easily ascertain the characteristics of the treatment tool 4 attached to the drive portion 5. Accordingly, on the basis of the identification information of the treatment tool 4 acquired from the manipulation input portion 10, the controller 12 can perform appropriate control for the treatment tool 4 in accordance with the type of that treatment tool 4. In addition, the surgeon can immediately ascertain which treatment tool 4 the manipulation input portion 10 is currently associated with, thus enabling intuitive manipulation.

For example, even in the case in which the treatment tool 4 is exchanged for another type of treatment tool 4, by allowing the controller 12 to acquire the identification information of the exchanged treatment tool 4, it is possible to ascertain the relationship between the manipulation input portion 10 and the exchanged treatment tool 4, and thus, it is possible to appropriately control the exchanged treatment tool 4. In other words, it is possible to easily switch between the treatment tools 4 in the controller 12, and it is possible to immediately manipulate the exchanged treatment tool 4 via the manipulation input portion 10.

Second Embodiment

A surgical manipulator system according to a second embodiment of the present invention will be described below with reference to the drawings. The surgical manipulator system according to this embodiment differs from the surgical manipulator system according to the first embodiment, described above in terms of the following points.

Figure 5:
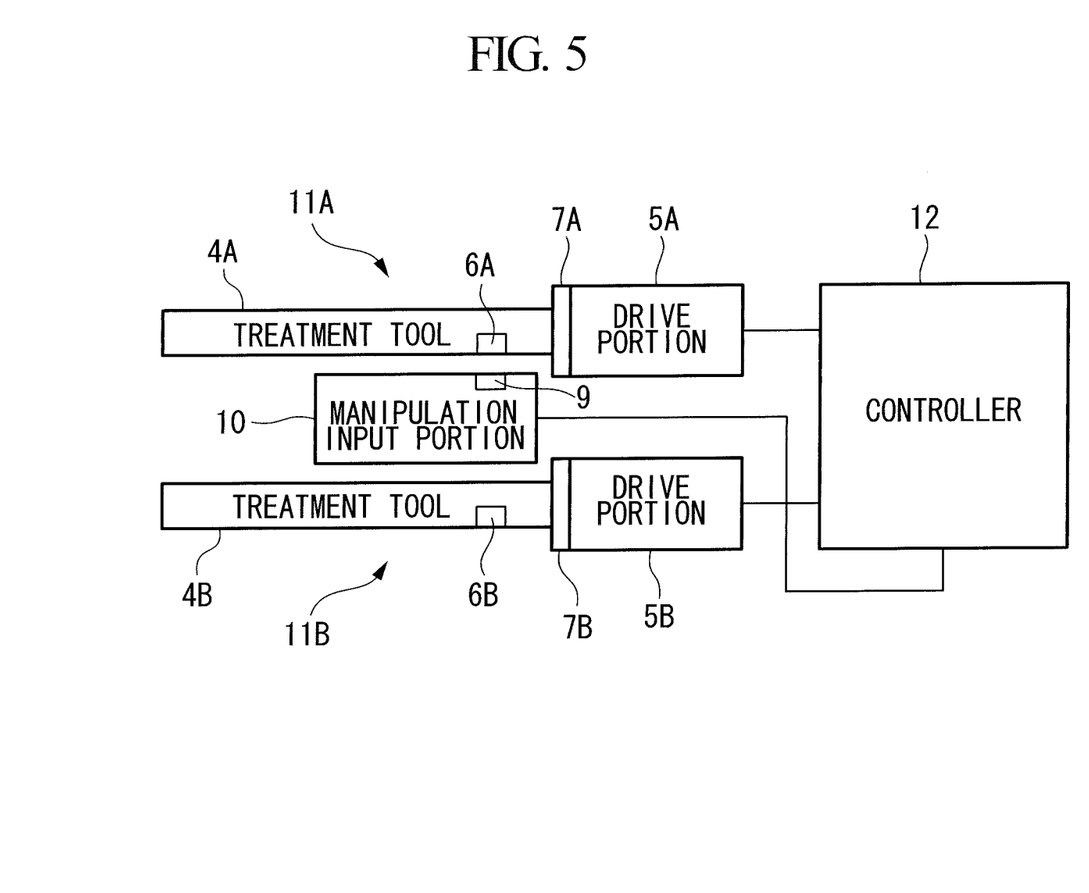
FIG. 5 is a diagram showing, in outline, the configuration of a surgical manipulator system according to a second embodiment of the present invention.

As shown in FIG. 5, the surgical manipulator system according to this embodiment is provided with a plurality of manipulators 11A and 11B (this embodiment will be described assuming that two manipulators are provided), and drive portions 5A and 5B of the individual manipulators 11A and 11B are provided with main-unit-side reading portions 7A and 7B that read identification information of the treatment tools 4A and 4B. In this embodiment, of the plurality of treatment tools 4A and 4B, the controller 12 associates a predetermined treatment tool with the manipulation input portion 10, and the treatment tool associated with the manipulation input portion 10 is controlled by the controller 12 in accordance with the instruction signals based on manipulation of the manipulation input portion 10.

The individual drive portions 5A and 5B of the manipulators 11A and 11B are provided with main-unit-side reading portions 7A and 7B that read the identification information of the treatment tools 4A and 4B, and, by attaching the treatment tools 4A and 4B to the drive portions 5A and 5B, the identification information of the treatment tools 4A and 4B can be read from identification-information retaining portions 6A and 6B of the treatment tools 4A and 4B.

The controller 12 associates the identification information of the treatment tools 4A and 4B read by the manipulation-side reading portion 9 with the identification information of the treatment tools 4A and 4B read by the main-unit-side reading portions 7A and 7B, and one of the drive portions 5A and 5B of the manipulators 11A and 11B to which the treatment tools 4A and 4B are connected is controlled on the basis of this correspondence relationship.

Figure 6:
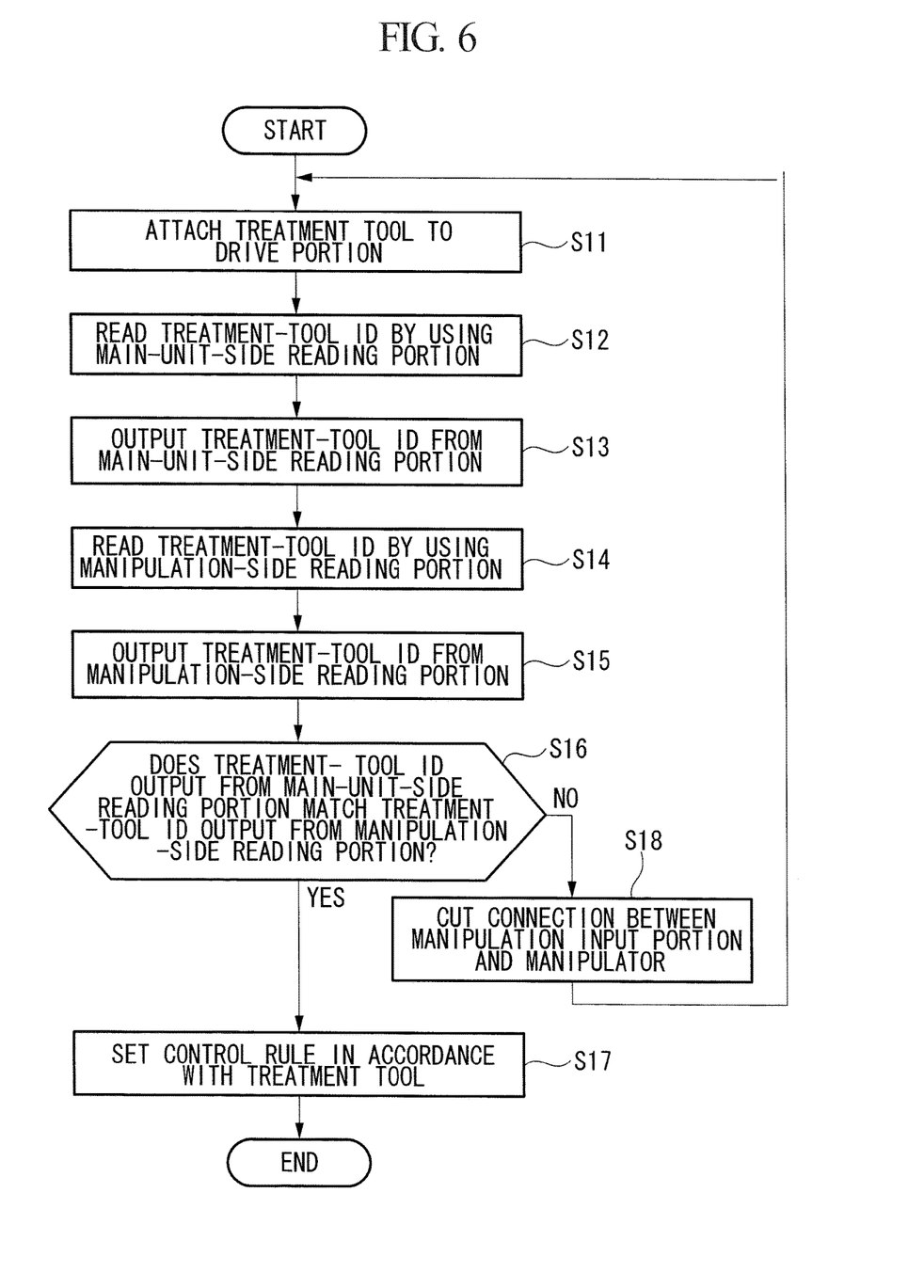
FIG. 6 is a flowchart showing the flow of processing when associating a manipulation input portion and a treatment tool in the surgical manipulator system according to the second embodiment of the present invention.

In the following, in accordance with the flowchart of FIG. 6, the manner in which the controller 12 judges the correspondence relationship among, that is, the manner in which the controller 12 associates, the identification information of the treatment tools 4A and 4B read by the manipulation-side reading portion 9, the identification information of the treatment tools 4A and 4B read by the main-unit-side reading portions 7A and 7B, and the drive portions 5A and 5B will be described. In the following descriptions, it is assumed that the treatment tool 4A is attached to the drive portion 5A of the manipulator 11A.

The treatment tool 4A is attached to the drive portion 5A of the desired manipulator 11A in step S11, and the identification information (indicated as "treatment-tool ID" in FIG. 6) of the treatment tool 4A stored in the identification-information retaining portion 6A of the treatment tool 4A is read by the main-unit-side reading portion 7A in step S12. The read identification information of the treatment tool 4A is output to the controller 12 in step S13 as the identification information of the treatment tool 4A attached to the drive portion 5A. By doing so, the controller 12 ascertains that the treatment tool attached to the manipulator 11A is the treatment tool 4A.

Next, in step S14, the manipulation input portion 10 is brought close to the treatment tool 4A attached to the drive portion 5A, and the manipulation-side reading portion 9 reads the identification information of the treatment tool 4A stored in the identification-information retaining portion 6A of the treatment tool 4A. The read identification information of the treatment tool 4A is output to the controller 12 in step S15 as the identification information of the treatment tool 4A that corresponds to the manipulation input portion 10. By doing so, the controller 12 ascertains that the treatment tool corresponding to the manipulation input portion 10 is the treatment tool 4A.

Because the controller 12 has ascertained the treatment tool 4A corresponding to the drive portion 5A and the treatment tool 4A corresponding to the manipulation input portion 10 by performing the above-described steps, in step S16, the identification information of the treatment tool 4A that has already been acquired by the main-unit-side reading portion 7A is compared with the identification information of the treatment tool 4A acquired by the manipulation-side reading portion 9, and it is judged whether or not the two sets of the identification information match each other. Regarding the manipulator for which the two sets of the identification information do not match each other as a result of the judgment, the connection between the manipulation input portion 10 and the manipulator is cut (the manipulator for which the identification information does not match is not actuated when inputs are made via the manipulation input portion 10. In other words, the manipulation input portion 10 is not connected with all of the manipulators, and only the associated manipulator is actuated.) (step S18).

When the two sets of the identification information match each other, the procedure proceeds to step S17, and the controller 12 sets the control rule in accordance with the treatment tool 4A. Here, the identification information read by the manipulation-side reading portion 9 and the identification information read by the main-unit-side reading portion 7A both are the identification information of the treatment tool 4A, and, because the two sets of identification information match each other, in step S17, the controller 12 sets the control rule in accordance with the treatment tool 4A, thus making it possible to control the drive portion 5 on the basis of the instruction signals from the manipulation input portion 10.

When switching the manipulation target of the manipulation input portion 10 from the treatment tool 4A to the treatment tool 43, processing of the above-described steps S11 to S18 is performed again; and, at the controller 12, it is ascertained that the treatment tool 4B is associated with the drive portion 5B and that the manipulation input portion 10 is associated with the treatment tool 4B, the identification information of the treatment tool 4B acquired by the main-unit-side reading portion 7B is compared with the identification information of the treatment tool 4B acquired by the manipulation-side reading portion 9, and it is judged whether or not the two sets of identification information match each other.

In this way, with this embodiment, even in the case in which a plurality of manipulators 11A and 113 are provided, by acquiring the identification information of the treatment tools 4A and 4B at the drive portions 5A and 5B, by acquiring the identification information of the treatment tools 4A and 4B at the manipulation input portion 10 also, and by comparing the two sets of identification information, it is possible to easily ascertain the relationship among the manipulation input portion 10, the manipulators 11A and 11B, and the treatment tools 4A and 4B attached to the drive portions 5A and 5B.

In other words, because it is possible to easily ascertain, at the controller 12, which type of treatment tool 4A or 4B is attached to which one of the plurality of manipulators 11A and 11B, it is possible to set, for the manipulator 11A or 11B to be controlled, the control rule corresponding to the treatment tool 4A or 4B attached to that manipulator 11A or 11B. In addition, the surgeon can immediately ascertain which one of the treatment tools 4A and 4B the manipulation input portion 10 is currently associated with, thus enabling intuitive manipulation.

(Modification)

Figure 7:
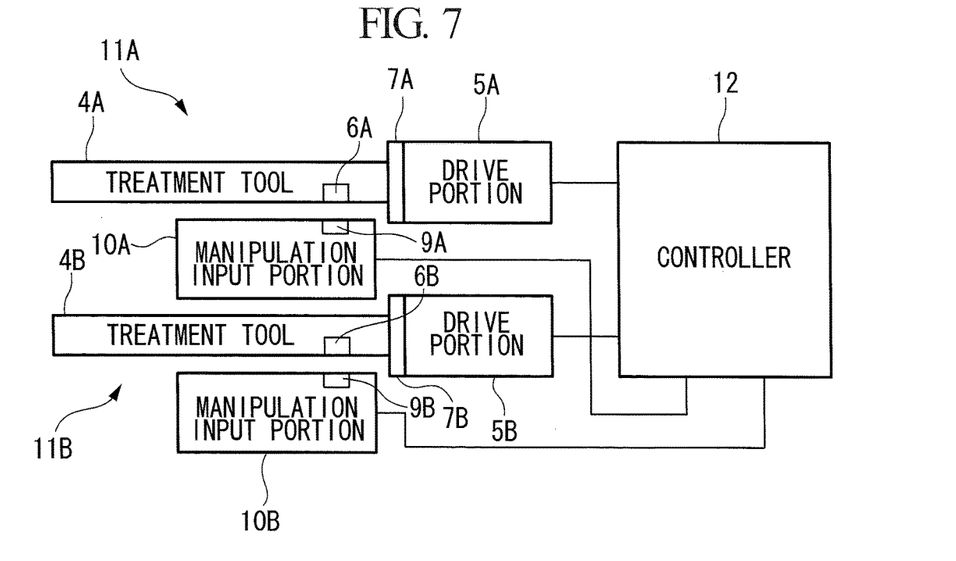
FIG. 7 is a diagram showing, in outline, the configuration of a surgical manipulator system according to a modification of the second embodiment of the present invention.
Figure 8:
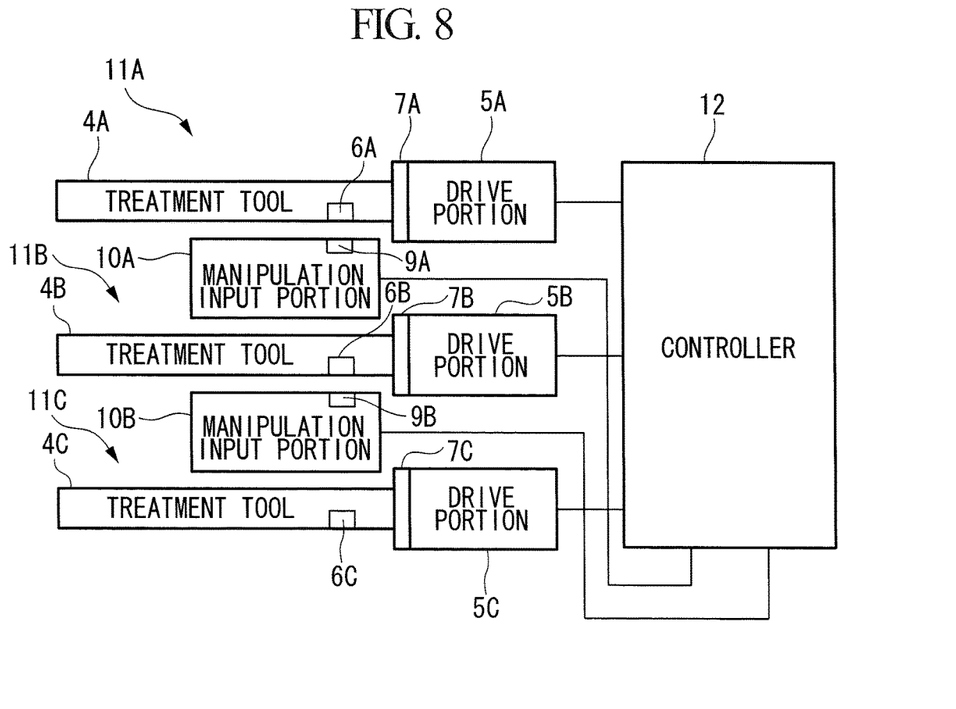
FIG. 8 is a diagram showing, in outline, the configuration of a surgical manipulator system according to a modification of the second embodiment of the present invention.

Although an example in which one manipulation input portion 10 is provided for two manipulators 11A and 11B has been described in the surgical manipulator system according to the second embodiment, described above, there is no limitation thereto. For example, it is possible to employ a configuration in which two manipulation input portions 10A and 10B and the two manipulators 11A and 11B are provided, as shown in FIG. 7, and it is also possible to provide three manipulators 11A, 11B, and 11C for the two manipulation input portions 10A and 10B, as shown in FIG. 8.

In this case also, main-unit-side reading portions 7A, 7B, and 7C of the manipulators 11A, 11B, and 11C acquire identification information of the treatment tools 4A, 4B, and 4C, manipulation-side reading portions 9A and 9B acquire the identification information of the treatment tools 4A, 4B, and 4C, and the controller 12 judges whether or not the two sets of identification information match each other. By doing so, it is possible to easily ascertain the correspondence relationship among the manipulation input portions 10A and 10B, the manipulators 11A, 11B, and 11C, and the treatment tools 4A, 4B, and 4C. In other words, it is possible to easily ascertain which type of treatment tool is attached to which one of the plurality of manipulators 11A, 11B, and 11C, and it is also possible to easily ascertain, of the plurality of manipulation input portions 10A and 10B, the manipulation input portion from which the instruction signals should be output.

Third Embodiment

A surgical manipulator system according to a third embodiment of the present invention will be described below with reference to the drawings. The surgical manipulator system according to this embodiment differs from the surgical manipulator system according to the first embodiment, described above, in terms of the following points.

Figure 9:
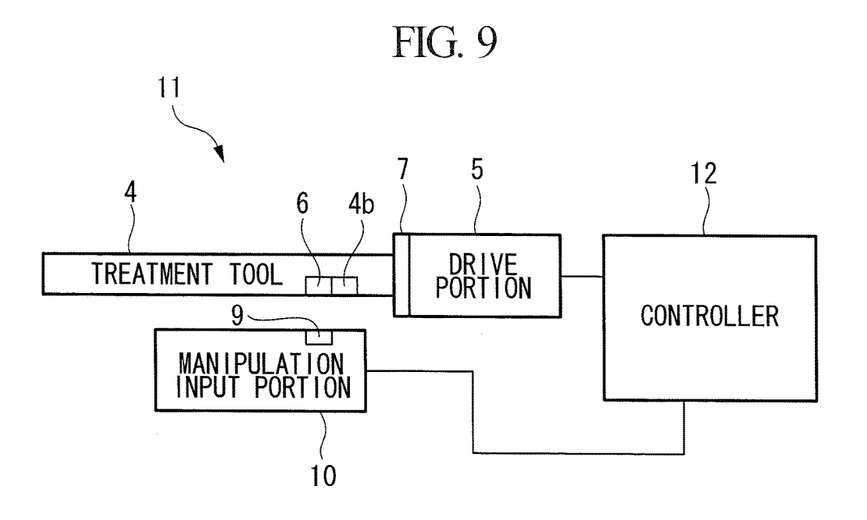
FIG. 9 is a diagram showing, in outline, the configuration of a surgical manipulator system according to a third embodiment of the present invention.

As shown in FIG. 9, with the surgical manipulator system according to this embodiment, the treatment tool reads the information from the controller 12 via the drive portion 5, and, by reading this information with the manipulation-side reading portion 9 of the manipulation input portion 10, the manipulation input portion consolidates all pieces of information.

Because of this, the treatment tool 4 is provided with a treatment-tool-side reading portion 4b that reads necessary information from the drive portion 5, and the manipulation-side reading portion 9 is configured so as to read predetermined information from the treatment-tool-side reading portion 4b. The controller 12 outputs, to the drive portions 5, connection information about to which connector of the controller 12 the drive portion 5 is connected, and the treatment-tool-side reading portion 4b reads the connection information.

Note that, as the connection information of the drive portion 5, voltage values or light can be employed. It is possible to identify to which connector of the controller 12 the drive portion 5 is connected by, in the case of the voltage values, varying the voltage values and by, in the case of light, varying the amount of light or the color of emitted light, for the individual connectors or control identifiers of the controller 12.

The manipulation-side reading portion 9 reads the connection information from the treatment-tool-side reading portion 4*b*, together with the identification information of the treatment tool 4, and outputs these pieces of information to the controller 12. The controller 12 controls the drive portion 5 by associating the drive portion 5 to which the treatment tool 4 is attached and the manipulation input portion 10 on the basis of the identification information and the connection information of the treatment tool 4 read by the manipulation-side reading portion 9.

As has been described above, because the manipulation-side reading portion 9 acquires all pieces of information required to associate the manipulation input portion 10 and the drive portion 5 to which the treatment tool 4 is attached, it is possible to suppress the occurrence of misrecognition.

(Modification)

The above-described third embodiment may employ a configuration in which individual drive portions 5 of a plurality of manipulators 11 store main-unit identification information, and the treatment tool is provided with the treatment-tool-side reading portion 4*b* that reads this main-unit identification information. In this case, the manipulation-side reading portion 9 is configured so as to read the main-unit identification information from the treatment-tool-side reading portion 4*b*. The controller 12 controls the drive portions 5 by associating the drive portions 5 with the manipulation input portion 10 on the basis of the identification information of the treatment tool 4 and the main-unit identification information read by the manipulation-side reading portion 9.

By doing so, because it is possible to set the control rule in accordance with built-in motors of the drive portions 5, for example, in the case in which the plurality of drive portions 5 are provided with different types of motors, it is possible to correct different properties in each motor. In addition, it is also possible to include the usage counts of the motors as the main-unit identification information.

Fourth Embodiment

Figure 10:
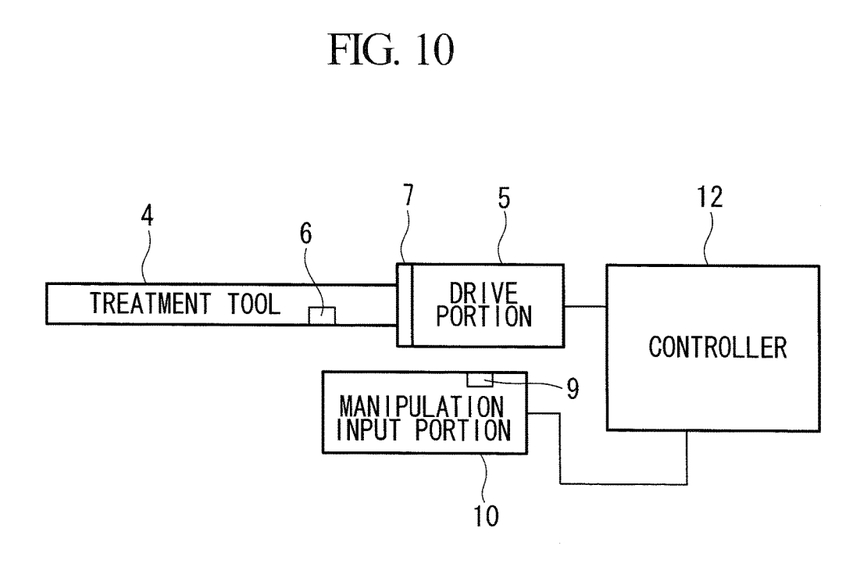
FIG. 10 is a diagram showing, in outline, the configuration of a surgical manipulator system according to a fourth embodiment of the present invention.

A surgical manipulator system according to a fourth embodiment of the present invention will be described below with reference to the drawings. With the surgical manipulator system according to the first embodiment, described above, the manipulation-side reading portion 9 communicates with the identification-information retaining portion 6 of the treatment tool 4 to read the identification information of the treatment tool 4; in this embodiment, however, the identification information of the treatment tool 4 is acquired from a main-unit-side reading portion 7 of the drive portion 5.

As shown in FIG. 10, the surgical manipulator system according to this embodiment is provided with, in the drive portion 5, the main-unit-side reading portion 7 that reads the identification information of the treatment tool 4. The main-unit-side reading portion 7 is configured so as to read the identification information of the treatment tool 4 from the identification-information retaining portion 6 of the treatment tool 4 when the treatment tool 4 is attached to the drive portion 5. In addition, the main-unit-side reading portion 7 acquires, from the controller 12, the connection information related to the connector to which the controller 12 is connected.

The manipulation-side reading portion 9 reads the connection information from the main-unit-side reading portion 7, together with the identification information of the treatment tool 4, and outputs these pieces of information to the controller 12. The controller 12 controls the drive portion 5 by associating the drive portion 5 to which the treatment tool 4 is attached and the manipulation input portion 10 on the basis of the identification information and the connection information of the treatment tool 4 read by the manipulation-side reading portion 9.

As has been described above, because the manipulation-side reading portion 9 acquires all pieces of information required to associate the manipulation input portion 10 and the drive portion 5 to which the treatment tool 4 is attached, it is possible to suppress the occurrence of misrecognition.

{0048}

Fifth Embodiment

Figure 11A:
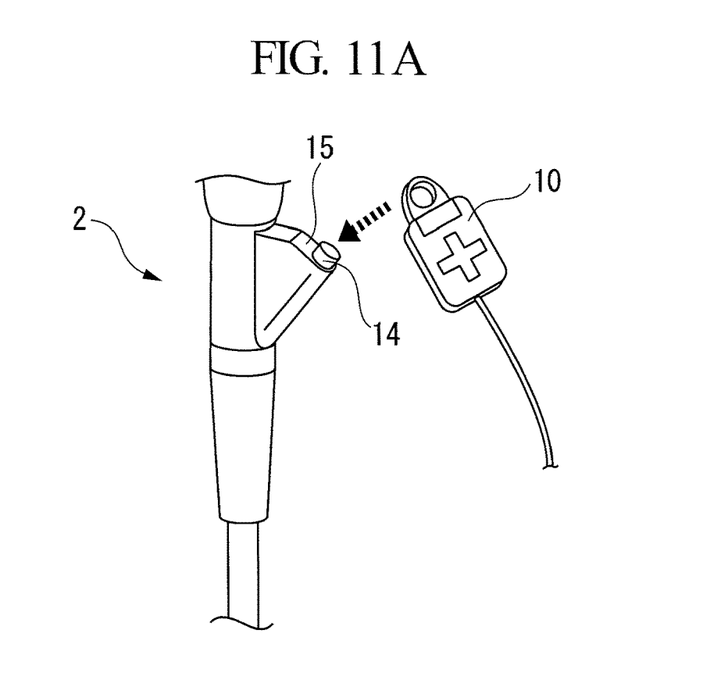
FIG. 11A is a diagram showing, in outline, the configuration of a surgical manipulator system according to a fifth embodiment of the present invention.
Figure 11B:
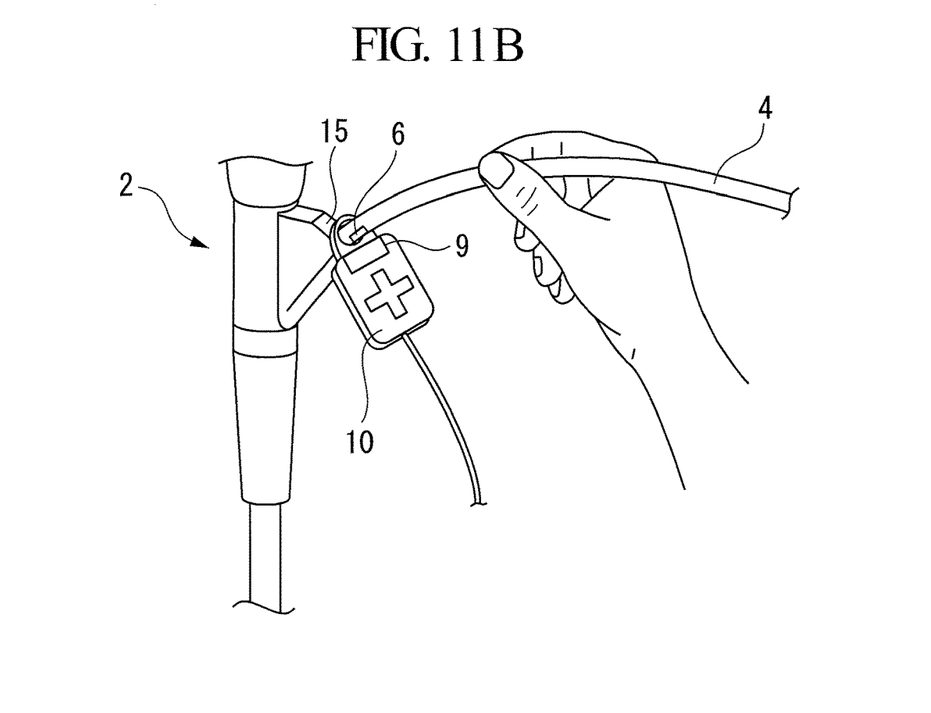
FIG. 11B is a diagram showing, in outline, the configuration of a surgical manipulator system according to a fifth embodiment of the present invention.

As shown in FIG. 11A, in this embodiment, a manipulation-input-portion attaching portion 15 to/from which the manipulation input portion 10 can be attached/detached is provided at an insertion port 14 of a forceps channel into which the treatment tool 4 of an endoscope 2 is inserted. Then, as shown in FIG. 11B, by inserting the treatment tool 4 into the forceps channel in the state in which the manipulation input portion 10 is attached to the manipulation-input-portion attaching portion 15, the identification-information retaining portion 6 of the treatment tool 4 and the manipulation-side reading portion 9 communicate with each other, the manipulation-side reading portion 9 reads the identification information of the treatment tool 4, and the identification information is output to the controller 12. The controller 12 controls the drive portion 5 on the basis of the identification information of the treatment tool 4 read by the manipulation-side reading portion 9.

By doing so, for example, in an endoscope 2 having a plurality of forceps channels, it is possible to easily ascertain which type of treatment tool 4 is inserted into which one of the forceps channels.

(Modification)

Figure 12:
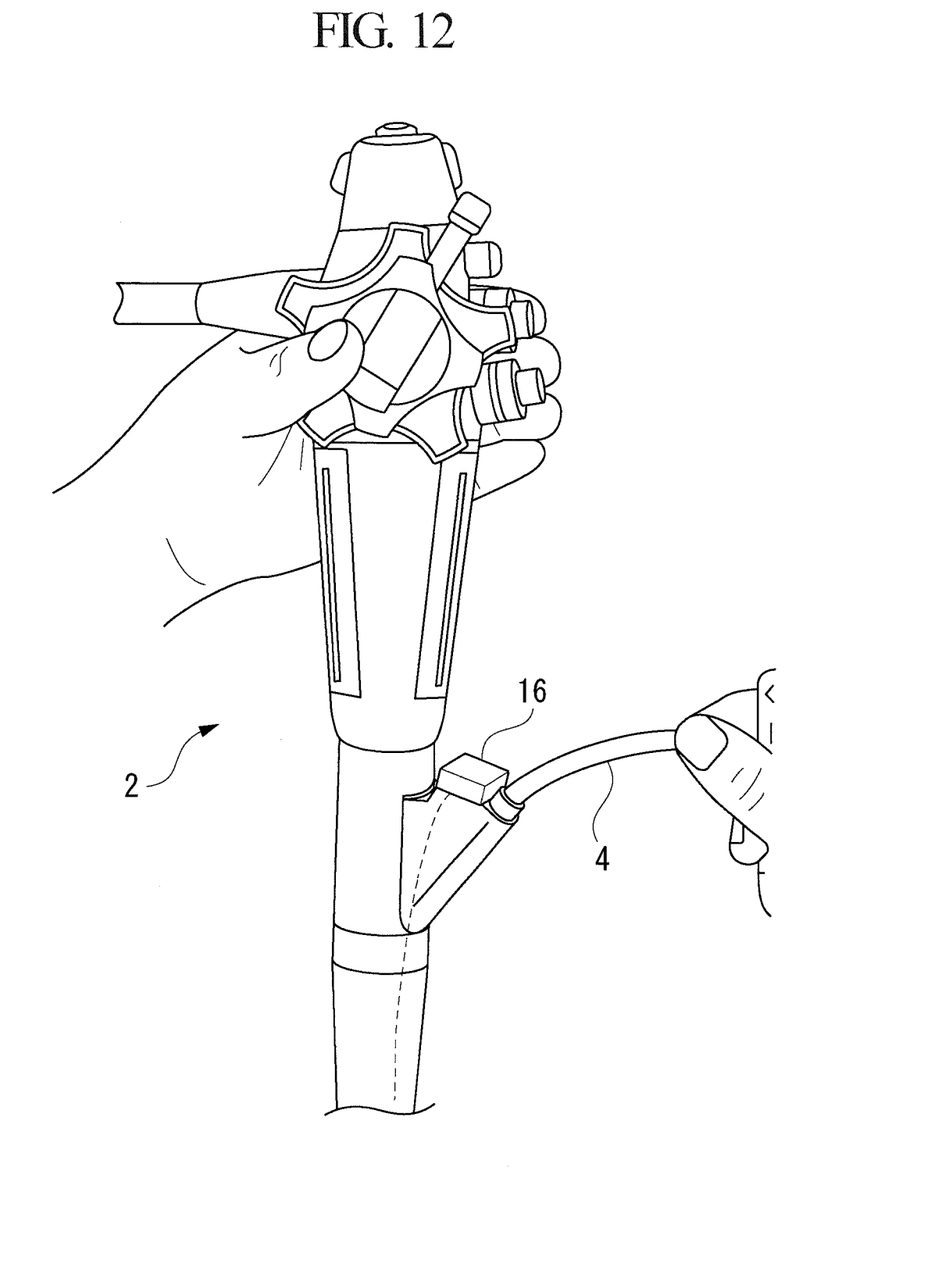
FIG. 12 is a diagram showing, in outline, the configuration of a surgical manipulator system according to a modification of the fifth embodiment of the present invention.

As shown in FIG. 12, it is possible to employ a configuration in which a channel-side reading portion 16 is provided, in advance, at an insertion port 14 of the forceps channel into which the treatment tool 4 of the endoscope 2 is inserted. In this case, when inserting the treatment tool 4 into the forceps channel, the identification-information retaining portion 6 of the treatment tool 4 and the channel-side reading portion 16 can communicate with each other, and the identification information of the treatment tool 4 can be read by the channel-side reading portion 16.

As a result, the above-described embodiments lead to the following aspects.

An aspect of the present invention is a surgical manipulator system including a manipulator provided with a treatment tool having at least one joint and a drive portion that is attached to the treatment tool to drive the treatment tool; a manipulation input portion with which manipulation for causing, by driving the drive portion of the manipulator, the treatment tool to perform desired operation is input; and a control portion that controls the drive portion on the basis of the manipulation that has been input via the manipulation input portion, wherein the treatment tool is provided with an identification-information retaining portion that retains identification information of the treatment tool, the manipulation input portion is provided with a manipulation-side reading portion that performs short-distance communication with the identification-information retaining portion of the treatment tool, thus reading the identification information of the treatment tool, and the control portion controls the drive portion on the basis of the identification information of the treatment tool read by the manipulation-side reading portion.

With the surgical manipulator system according to this aspect, when controlling the manipulator in accordance with the manipulation of the manipulation input portion, the manipulation-side reading portion reads the identification information of the treatment tool from the identification-information retaining portion of the treatment tool attached to the manipulator, and the control portion controls the drive portion on the basis of the identification information of the treatment tool acquired by the manipulation-side reading portion. Therefore, the control portion can ascertain the relationship between the manipulation input portion and the treatment tool provided in the manipulator, that is, the treatment tool to be controlled on the basis of the manipulation of the manipulation input portion, the type of that treatment tool, or the like. Thus, it is possible to perform control by setting an appropriate control rule for the treatment tool in accordance with the type of that treatment tool. In other words, without requiring bothersome setting manipulation and switching manipulation performed by a surgeon, it is possible to intuitively associate the manipulation input portion to be manipulated and the treatment tool driven by the manipulator.

In the above-described aspect, it is preferable that more than one of the manipulator be provided, wherein each of the drive portions is provided with a main-unit-side reading portion that reads the identification information of the treatment tool, and the control portion controls the drive portion on the basis of the identification information of the treatment tool read by the manipulation-side reading portion and a correspondence relationship between the identification information of the treatment tool read by the main-unit-side reading portion and the drive portion.

By doing so, because the identification information of the treatment tool is acquired by the drive portion and the identification information of the treatment tool is also acquired by the manipulation input portion, even if a plurality of manipulators are provided, it is possible to easily ascertain the relationship among the manipulation input portion, the drive portion, and the treatment tool attached to the drive portion.

In the above-described aspect, it is preferable that more than one of the manipulation input portion be provided, wherein the control portion controls the drive portion on the basis of a correspondence relationship between the identification information of the treatment tool read by the manipulation-side reading portion and the manipulation input portion and the correspondence relationship between the identification information of the treatment tool read by the main-unit-side reading portion and the drive portion.

By doing so, even in the case in which a plurality of manipulation input portions and a plurality of manipulators are provided, it is possible to easily ascertain the relationship among the manipulation input portion, the drive portion, and the treatment tool attached to the drive portion on the basis of the identification information read between each other.

In addition, in the above-described aspect, the control portion may set a correspondence relationship between manipulation of the manipulation input portion and operation of the drive portion on the basis of the identification information of the treatment tool read by the manipulation-side reading portion.

By doing so, a surgeon can appropriately manipulate the manipulation input portion in accordance with the type of the treatment tool, and the control portion can control the drive portion in accordance with the treatment tool and in accordance with the manipulation that has been input via the manipulation input portion.

In addition, in the above-described aspect the control portion may store the identification information of the treatment tool read by the manipulation-side reading portion and usage state of the treatment tool in association with each other.

By doing so, it is possible to manage the information about the treatment tool in greater details.

In the above-described aspect, the drive portion may hold main-unit identification information, the treatment tool may be provided with an information receiving portion that receives the main-unit identification information, the manipulation-side reading portion may read the main-unit identification information received by the information receiving portion, and the control portion may control the drive portion on the basis of the identification information of the treatment tool and the main-unit identification information read by the manipulation-side reading portion.

As has been described above, by reading both of the identification information of the treatment tool and the main-unit identification information by using the manipulation-side reading portion, because the manipulation-side reading portion acquires all pieces of information required to associate the manipulation input portion and the drive portion to which the treatment tool is attached, it is possible to suppress the occurrence of misrecognition.

An aspect of the present invention provides a surgical manipulator system including a manipulator provided with a treatment tool having at least one joint and a drive portion that is attached to the treatment tool to drive the treatment tool; a manipulation input portion with which manipulation for causing, by driving the drive portion of the manipulator, the treatment tool to perform desired operation is input; and a control portion that controls the drive portion on the basis of the manipulation that has been input via the manipulation input portion, wherein the treatment tool is provided with an identification-information retaining portion that retains identification information of the treatment tool, the drive portion is provided with a main-unit-side reading portion that reads the identification information of the treatment tool, and retains main-unit identification information, which is the identification information of the drive portion, the manipulation input portion is provided with a manipulation-side reading portion that performs short-distance communication with the main-unit-side reading portion of the drive portion, thus reading the identification information of the treatment tool and the main-unit identification information, and the control portion controls the drive portion on the basis of the identification information of the treatment tool and the main-unit identification information read by the manipulation-side reading portion.

With this aspect, when controlling the manipulator in accordance with the manipulation of the manipulation input portion, the manipulation-side reading portion reads the identification information of the treatment tool attached to the drive portion, read by the main-unit-side reading portion, and the main-unit identification information retained by the drive portion, and the control portion controls the drive portion on the basis of the identification information of the treatment tool and the main-unit identification information acquired by the manipulation-side reading portion. Therefore, the control portion can ascertain the relationship between the manipulation input portion and the treatment tool and the drive portion provided in the manipulator, that is, the treatment tool to be controlled on the basis of the manipulation that has been input via the manipulation input portion, the type of that treatment tool, or the like. Thus, it is possible to perform control by setting an appropriate control rule for the treatment tool in accordance with the type of that treatment tool.

In addition, the above-described aspect may be provided with an endoscope having a forceps channel into which the treatment tool is inserted, wherein the endoscope may be provided with, at an insertion port of the forceps channel for the treatment tool, a manipulation-input-portion attaching portion to/from which the manipulation input portion can be attached/detached.

With this aspect, when the manipulation input portion is attached to the master attaching portion and the treatment tool is inserted into the insertion port of the forceps channel, the identification information of the treatment tool attached to the drive portion is read by the manipulation-side reading portion. Therefore, in an endoscope having a plurality of forceps channels, it is possible to easily ascertain which type of treatment tool is inserted into which one of the forceps channels.

The present invention affords an advantage in that it is possible to, without having to perform a bothersome setting operation or switching operation, intuitively associate a manipulation input portion to be manipulated and a treatment tool that a drive portion drives.

REFERENCE SIGNS LIST 2 endoscope
3 inserted portion
4, 4A, 4B, 4C treatment tool
4b treatment-tool-side reading portion
5, 5A, 5B, 5C drive portion
6, 6A, 6B, 6C identification-information retaining portion
7, 7A, 7B, 7C main-unit-side reading portion
8 manipulating portion
9, 9A, 9B manipulation-side reading portion
10, 10A, 10B manipulation input portion
11, 11A, 11B, 110 manipulator
12 controller
15 manipulation-input-portion attaching portion

The invention claimed is:

1. A surgical manipulator system comprising:
a manipulator comprising:
a treatment tool; and
a motor coupled to the treatment tool, the motor being configured to drive the treatment tool;
an input device configured to operate the manipulator;
a controller configured to control the motor based on an operation of the input device by an operator, the controller being configured to:
receive first identification information of the treatment tool via the input device, the first identification information being received from the manipulator;
receive second identification information of the motor via the input device, the second identification information being received from the manipulator; and
control the motor based on both the first identification information and the second identification information.

2. A surgical manipulator system according to claim 1, further comprising: more than one of the manipulators, wherein each of the drive portions is provided with a main-unit-side reading portion that reads the identification information of the treatment tool, and the control portion controls the drive portion on the basis of the identification information of the treatment tool read by the manipulation-side reading portion and a correspondence relationship between the identification information of the treatment tool read by the main-unit-side reading portion and the drive portion.

3. A surgical manipulator system according to claim 2, further comprising: more than one of the manipulation input portions; wherein the control portion controls the drive portion on the basis of a correspondence relationship between the identification information of the treatment tool read by the manipulation-side reading portion and the manipulation input portion and the correspondence relationship between the identification information of the treatment tool read by the main-unit-side reading portion and the drive portion.

4. The surgical manipulator system according to claim 1, wherein the controller is configured to set a correspondence relationship between an operation of the input device and an operation of the motor based on the first identification information.

5. The surgical manipulator system according to claim 1, wherein the controller is configured to:
associate the first identification information with a usage status of the treatment tool; and
store the first identification information and the usage status of the treatment tool.

6. The surgical manipulator system according to claim 1, further comprising:
an endoscope comprising:
a channel, the treatment tool being configured to be inserted into the channel;
a proximal port of the channel being configured to be detachably attached to the input device.

7. A surgical manipulator system comprising:
a manipulator comprising:
a treatment tool; and
a motor coupled to the treatment tool, the motor being configured to drive the treatment tool;
an input device configured to operate the manipulator;
an endoscope comprising:
a channel, the treatment tool being configured to be inserted into the channel;
a proximal port of the channel being configured to be detachably attached to the input device;
a controller configured to control the motor based on an operation of the input device by an operator, the controller being configured to:
receive first identification information of the treatment tool via the input device, the first identification information being received from the manipulator; and
control the motor based on the first identification information.

8. The surgical manipulator system according to claim 7, wherein the controller is configured to:
receive second identification information of the motor via the input device, the second identification information being received from the manipulator; and
control the motor based on both the first identification information and the second identification information.

9. The surgical manipulator system according to claim 7, wherein the controller is configured to set a correspondence relationship between an operation of the input device and an operation of the motor based on the first identification information.

10. The surgical manipulator system according to claim 7, wherein the controller is configured to:
associate the first identification information with a usage status of the treatment tool; and store the first identification information and the usage status of the treatment tool.

* * * * *